US010012568B1

(12) United States Patent
Backes et al.

(10) Patent No.: US 10,012,568 B1
(45) Date of Patent: Jul. 3, 2018

(54) BIBLADE SAMPLER

(71) Applicant: The United States of America as Represented by the Administrator of NASA, Washington, DC (US)

(72) Inventors: Paul G. Backes, La Crescenta, CA (US); Mircea Badescu, La Canada Flintridge, CA (US); Nicholas Wiltsie, Glendale, CA (US); Scott J. Moreland, Pasadena, CA (US); Jesse A. Grimes-York, Altadena, CA (US); Harish Manohara, Glendora, CA (US); Youngsam Bae, Placentia, CA (US); Risaku Toda, La Crescenta, CA (US); Russell G. Smith, Los Angeles, CA (US); Christopher McQuin, Mountain View, CA (US)

(73) Assignee: The United States of America as Represented by the Administrator of the National Aeronautics and Space Administration, Washington, DC (US)

( * ) Notice: Subject to any disclaimer, the term of this patent is extended or adjusted under 35 U.S.C. 154(b) by 162 days.

(21) Appl. No.: 15/219,032

(22) Filed: Jul. 25, 2016

Related U.S. Application Data

(60) Provisional application No. 62/199,419, filed on Jul. 31, 2015.

(51) Int. Cl.
*G01N 1/08* (2006.01)
*E21B 49/02* (2006.01)
*B66C 3/14* (2006.01)

(52) U.S. Cl.
CPC .................. *G01N 1/08* (2013.01); *B66C 3/14* (2013.01); *E21B 49/02* (2013.01); *G01N 2001/085* (2013.01)

(58) Field of Classification Search
CPC .. G01N 1/02; G01N 1/04; G01N 1/08; G01N 2001/085; B66C 3/14; B66C 3/16; B66C 3/18; E21B 49/02; E21B 49/025
See application file for complete search history.

(56) References Cited

U.S. PATENT DOCUMENTS

| 1,477,679 A | * | 12/1923 | Edward Woolley | ...... B66C 3/08 37/184 |
| 3,572,129 A | * | 3/1971 | Walthier et al. | ...... E21B 49/025 37/187 |
| 4,373,278 A | * | 2/1983 | Myrick | ................. E02F 3/4131 37/184 |

* cited by examiner

*Primary Examiner* — Justin Olamit
(74) *Attorney, Agent, or Firm* — Mark Homer

(57) ABSTRACT

A BiBlade sampler may include a first blade and a second blade in a retracted position. The BiBlade sampler may also include a gripper, which is driven by an actuator. The gripper may include a plurality of fingers to force the first blade and the second blade to remain in a retracted position. When the fingers are unhooked, the first blade and the second blade penetrate a surface of an object.

18 Claims, 7 Drawing Sheets

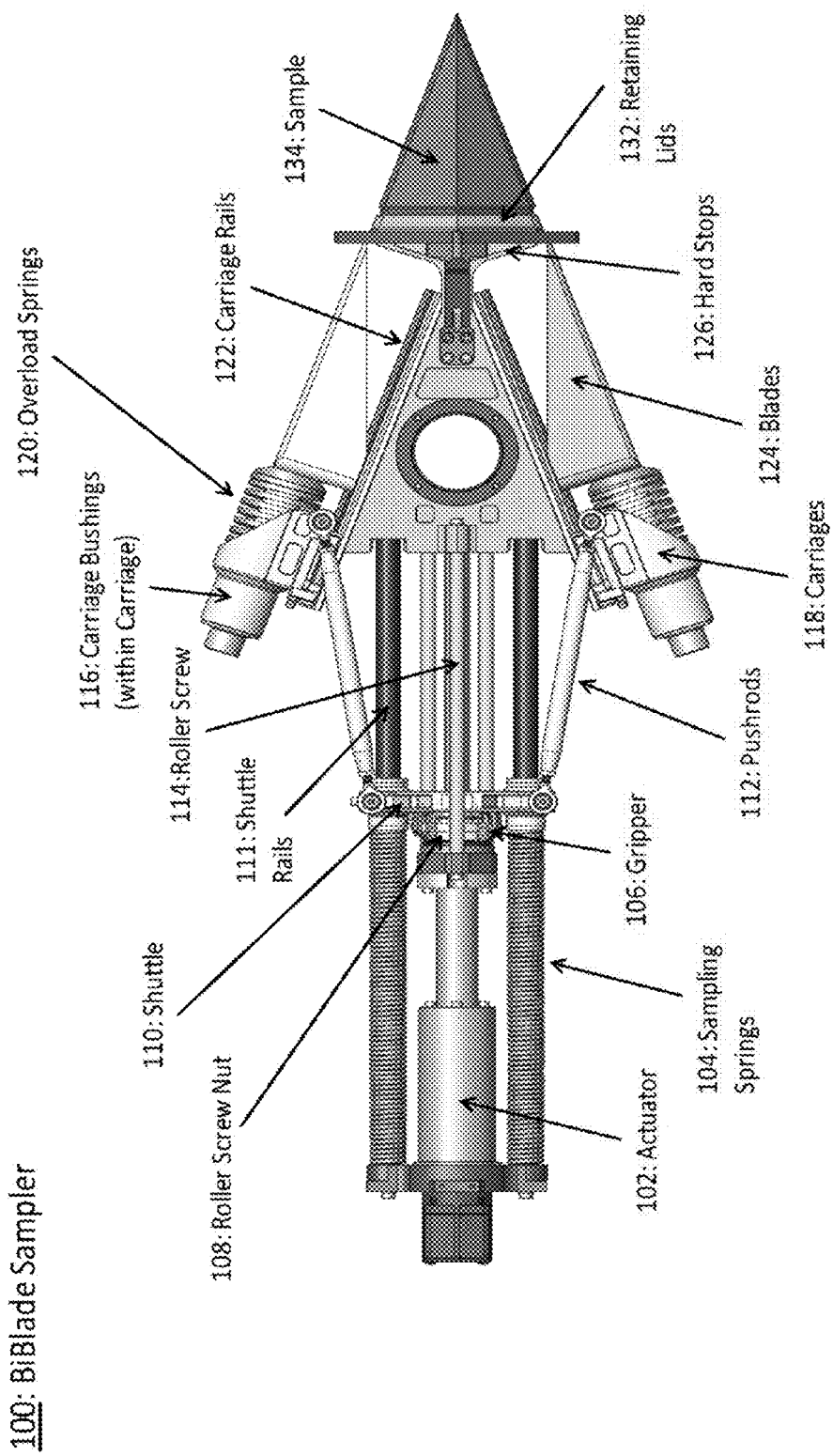

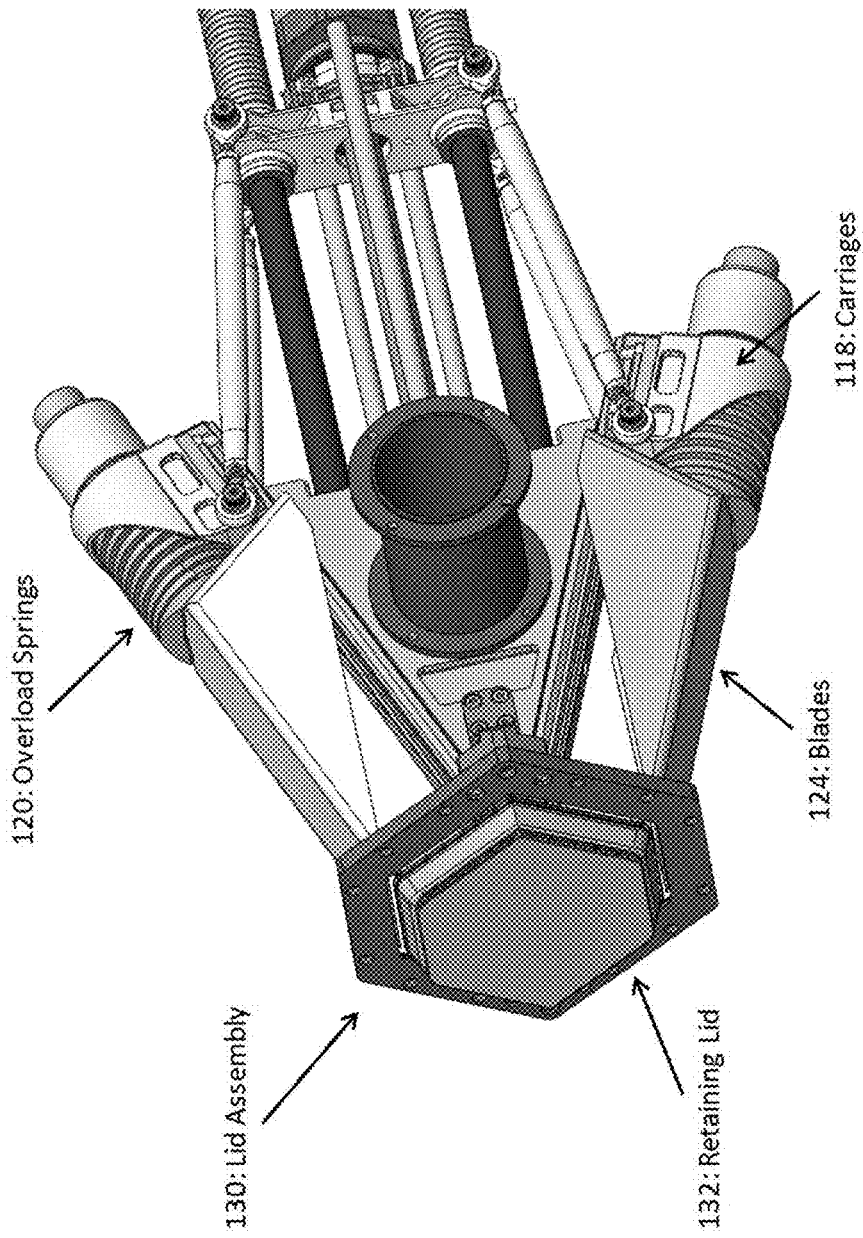

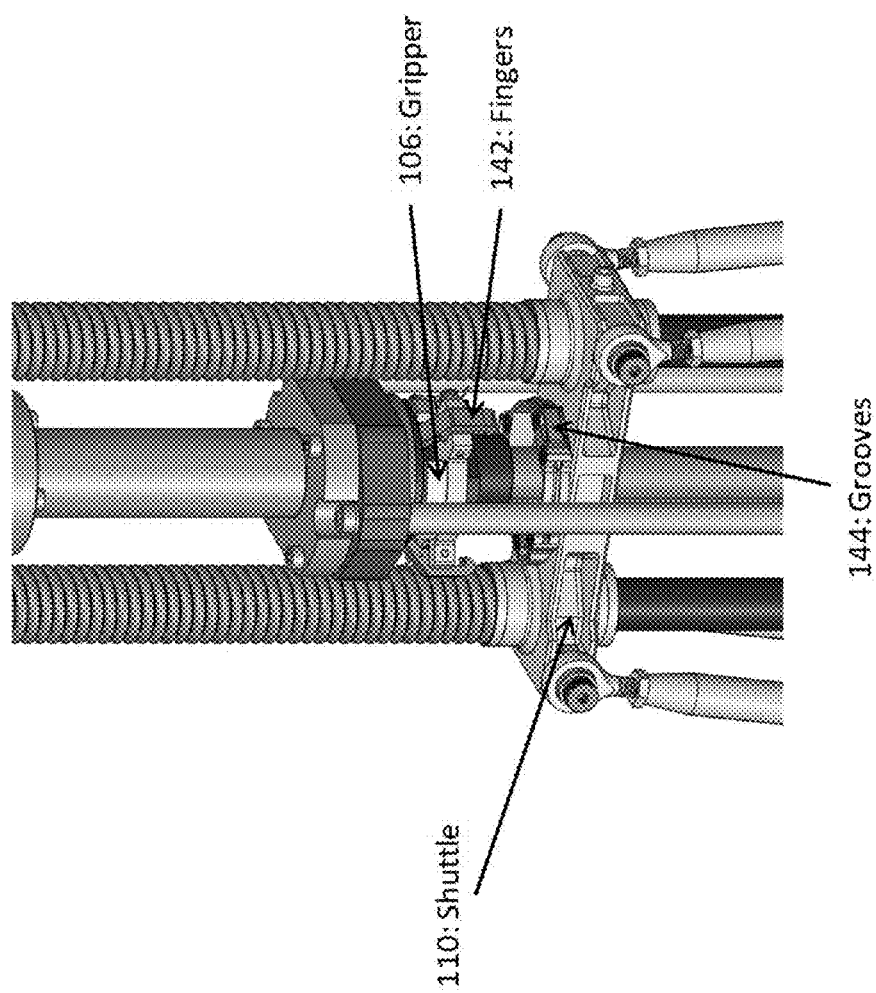

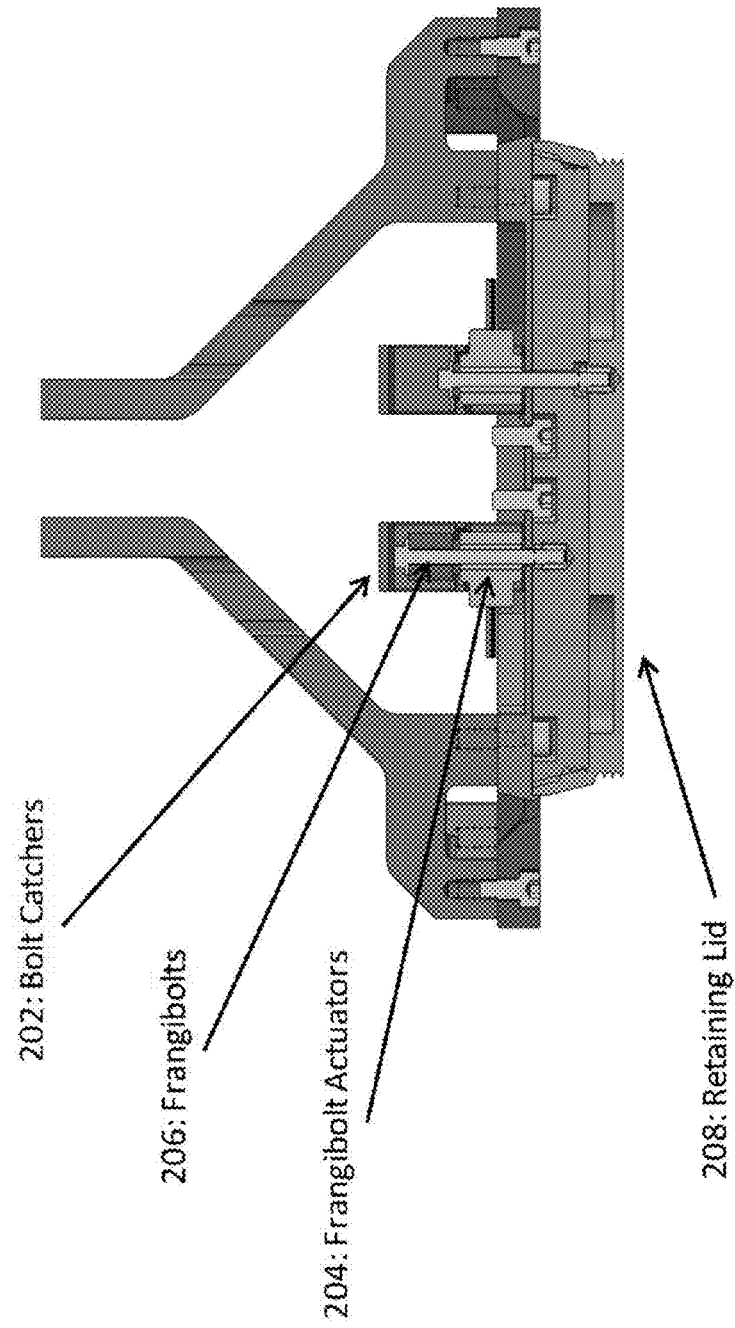

400: Sample Measurement Station

500

BIBLADE SAMPLER

CROSS-REFERENCE OF RELATED APPLICATION

This application claims the benefit of U.S. Provisional Application Ser. No. 62/199,419 filed on Jul. 31, 2015. The subject matter of this earlier filed provisional patent application is hereby incorporated by referenced in its entirety.

ORIGIN OF THE INVENTION

Embodiments of the present invention described herein were made in the performance of work under NASA contract NASI-03001 and are subject to the provisions of Public Law #96-517 (35 U.S.C. § 202) in which the Contractor has elected not to retain title.

FIELD

The present invention generally pertains to a BiBlade sampler, and more particularly, to a BiBlade sampler for acquiring samples from the surface of an object, as well as approaches for associated sample measurement and storage.

BACKGROUND

Various sampling techniques have been proposed for small body missions. These sampling techniques are associated with mission architectures. Mission architectures include lander, harpoon, dart, and touch-and-go (TAG).

Lander Architecture Mission.

In a lander architecture mission, a spacecraft would land and anchor to the surface of a planetary or moving object, and then a sampling tool would be deployed to the surface to acquire a sample. The lander architecture mission allows for the sampling process to take longer than for other mission architectures. For example, the Rosetta mission is a lander architecture in-situ sampling mission to comet 67P/Churyumov-Gerasimenko. The mission was launched by the European Space Agency in 2004 and arrived at the comet in August 2014. Its Philae robotic lander was planned to separate from the Rosetta orbiter spacecraft, land on and anchor to the comet, and then deploy a drill to acquire samples for in-situ analysis. The sampling drill weighs 5 kg, can penetrate up to 250 mm, and can acquire samples at predetermined depths inside its drill bit. The samples can then be transported to a carousel with 25 ovens. The drill was designed to penetrate material with strength ranging from fluffy snow to materials with a strength approaching a few MPa.

Harpoon Architecture Mission

In a harpoon architecture mission, a spacecraft would maneuver to the proximity of a small body surface, e.g., 10 m to 1 km from the surface. A sampler would then be shot to the surface with a tether connecting the sampler to the spacecraft. The momentum of the sampler would embed the sampler into the surface driving the material into the sampler. The sampler would then be ejected from the surface, and would be reeled back to the spacecraft with the tether. However, controlling the tether may be challenging.

Dart Architecture Mission

The dart architecture mission is similar to a harpoon architecture mission, except that there is no tether connecting the sampler to the spacecraft. In the dart architecture mission, the sampler is shot to the surface, and the sampler's kinetic energy is used to drive the sampler into the surface. A sample canister is then ejected from the surface, and the spacecraft would rendezvous with and capture the sample canister.

While the dart architecture mission eliminates the problems associated with controlling a tether, the dart architecture mission adds complexity of tracking, rendezvous, and capturing of the sample canister.

Tag Architecture Mission

In a TAG architecture mission, a spacecraft maneuvers within a few meters of the small body surface, and a robotic arm deploys a sampling tool to the surface. The sample in a TAG architecture mission is quickly acquired, and the spacecraft is then thrusted away. The sample can then be transferred to the spacecraft using the robotic arm.

Thus, a sampling technique for the TAG architecture mission may be beneficial.

SUMMARY

Certain embodiments of the present invention may be implemented and provide solutions to the problems and needs in the art that are outside the capabilities of conventional sample retrieval techniques. For instance, some embodiments pertain to a BiBlade sampler for the TAG mission architecture. The BiBlade sampler may be deployed to the surface of an object using a robotic arm in some embodiments.

In one embodiment, an apparatus includes a first blade and a second blade in a retracted position. The apparatus also includes a gripper. The gripper includes a plurality of fingers (or latches) to hold the first blade and the second blade in the retracted position. When the fingers are unhooked, the first blade and the second blade penetrate a surface of an object.

In another embodiment, a BiBlade sampler includes capturing a sample from an object. The BiBlade sampler may include a gripper that latches on to a shuttle using a plurality of fingers. The BiBlade sampler may also include an actuator that pulls the shuttle to a release point, causing a set of blades to move to a retracted position. The set of blades are connected to the shuttle via a set of push rods, and when the shuttle reaches the release point, the plurality of fingers releases the shuttle, causing the set of blades to move to a final position.

BRIEF DESCRIPTION OF THE DRAWINGS

In order that the advantages of certain embodiments of the invention will be readily understood, a more particular description of the invention briefly described above will be rendered by reference to specific embodiments that are illustrated in the appended drawings. While it should be understood that these drawings depict only typical embodiments of the invention and are not therefore to be considered to be limiting of its scope, the invention will be described and explained with additional specificity and detail through the use of the accompanying drawings, in which:

FIG. 1A is diagram illustrating a BiBlade sampler, according to an embodiment of the present invention.

FIG. 1B is a perspective view illustrating a BiBlade sampler, according to an embodiment of the present invention.

FIG. 1C is a perspective view illustrating a gripper and shuttle of the BiBlade sampler, according to an embodiment of the present invention.

FIG. 2 is a cross-sectional view illustrating a lid assembly, according to an embodiment of the present invention.

DETAILED DESCRIPTION OF THE EMBODIMENTS

Figure 3:
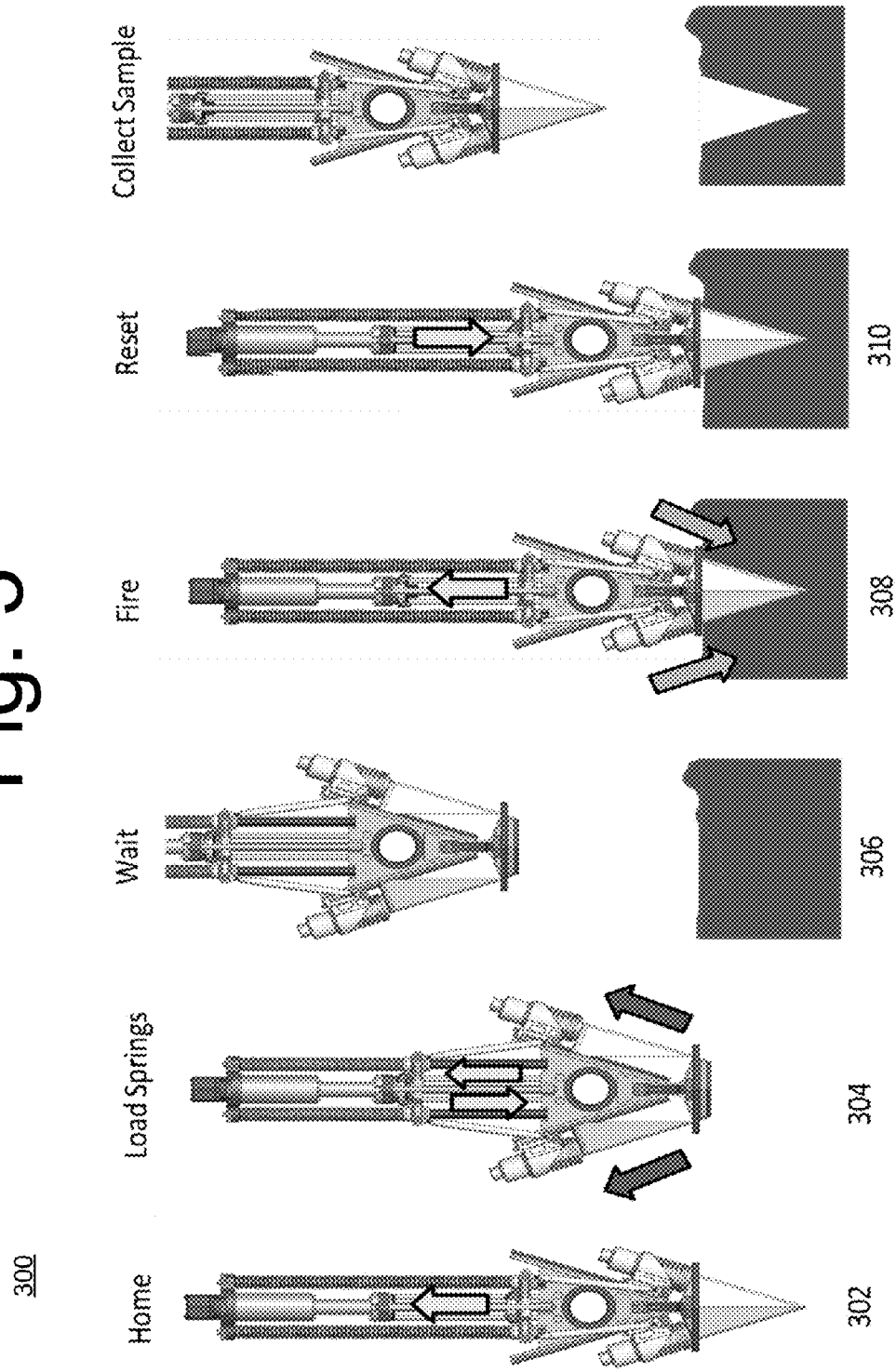
FIG. 3 illustrates a process for collecting a sample from an object, according to an embodiment of the present invention.

A BiBlade sampler may be used in a TAG mission architecture. For example, BiBlade sampler may be deployed to the surface of an object using a robotic arm. The object may be a planet, an asteroid, a comet, or any other object that would be appreciated by a person of ordinary skill in the art. In certain embodiments, BiBlade sampler may include two blades. The blades may be driven into the surface using springs, with the sampling action completed in approximately 0.1 seconds. This may allow the spacecraft to thrust away from the surface immediately upon initiation of the sampling action.

While closed, the blades may temporarily encapsulate the sample before sample measurement and final deposition of the sample in the sample vault of an Earth reentry vehicle (hereinafter "vehicle"). For example, the robotic arm may transfer the BiBlade sampler to a sample measurement station. The sample measurement station may include sample measurement chamber. The sample may be measured within the measurement chamber using a multi-fiberscope sample imager system.

Once the sample is measured, the robotic arm may move the BiBlade sampler to a sample vault of the vehicle. Upon placement of the sample within the sample vault, a lid attached to the BiBlade sampler may be released over the sample vault to encapsulate and/or secure the sample within the sample vault. The blades may be retracted, and the robotic arm may then move the BiBlade sampler away from the sample vault.

The robotic arm in some embodiments has three degrees-of-freedom (DOF). This may allow the robotic arm to deploy the BiBlade sampler to the surface, transfer the sample to the measurement station, and finally, transfer the sample to a sample vault of the vehicle. The attachment of the robotic arm allows the reacted forces during sampling to react through the spacecraft center of mass so sampling forces safely push the spacecraft away from the surface during the sampling event. In some embodiments, sample measurement may be performed in the vehicle's sample vault or in a separate sample measurement station.

FIG. 1A is diagram illustrating a BiBlade Sampler 100, according to an embodiment of the present invention. In some embodiments, BiBlade Sampler 100 includes two Blades (e.g., a first blade and a second blade) 124 and an Actuator 102. Blades 124 may have different cross-section shapes. For example, in FIG. 1B, Blades 124 have linear sides. In an alternative embodiment, Blades 124 may have curved sides, e.g., a continuous circular cross-section. This may be considered as cylindrical blades, where the shape of the blades is generated by slicing through a cylinder, for example. Actuator 102 may include a motor, which provides rotational motion and a resolver or encoder, which may provide measurement of the rotation of the motor shaft.

Roller Screw 114 may provide a threaded shaft that rotates with the actuator shaft. Roller Screw Nut 108 may ride up and down the Roller Screw 114 due to rotation of the Roller Screw 114 and thus translate rotational Actuator 102 shaft motion into linear motion of the Roller Screw Nut 108.

Actuator 102 may drive a Gripper 106 to latch onto Blades 124 via Shuttle 110. In some embodiments, Gripper 106 may passively lock onto Shuttle 110, pulling Shuttle 110 along Shuttle Rails 111. See, for example, FIG. 1C, which is a perspective view illustrating a Gripper 106 and Shuttle 110 of BiBlade sampler 100, according to an embodiment of the present invention.

Gripper 106 in some embodiments may include a plurality of Fingers 142 that may connect to Grooves 144 of Shuttle 110. This allows Gripper 106 to passively lock onto Shuttle 110, allowing Actuator 102 to retract Blades 124. In FIG. 1C, Fingers 142 are shown in a position prior to connecting or latching onto Grooves 144 of Shuttle 110. This may also be the position after releasing Fingers 142 from Grooves 144 of Shuttle 110, allowing Blades 124 to forcefully penetrate the surface of the object. Once Gripper 106 is pulled back to a certain point (i.e., the end of travel), the top of Fingers 142 is pressed to unhook Fingers 142 from Grooves 144. For example, the placement of Actuator 102 presses Fingers 142 when Gripper 106 is pulled back to the release point. This may release Shuttle 110 from Gripper 106. Stated another way, Actuator 102 allows Fingers 142 to latch onto to Shuttle 110, and also allow Fingers 142 to unlatch from Shuttle 110 when Shuttle 110 is pulled back to a certain point.

As shown in FIGS. 1A and 1B, once Gripper 106 is locked with Shuttle 110, Actuator 102 pulls or retracts Gripper 106 and Shuttle 110. As Gripper 106 and Shuttle 110 are pulled, Sampling Springs 104 are compressed and Pushrods 112, which are attached to sampling Blades 124, pull sampling Blades 124 to set sampling Blades 124 in an initial (or retracted) position.

In some embodiments, during compression of Sampling Springs 104, the Fingers 142 may be held 5 mm from their release point. For example, Gripper 106 may be pulled back to the release point of Fingers 142. When Fingers 142 are at the release point, Fingers 142 of Gripper 106 are released, releasing Shuttle 110. This results in compressed Sampling Springs 104 to push Shuttle 110 and Pushrods 112 forward. The movement of Pushrods 112 may cause Blades 124 to be pushed forward to a final (or closed) position. The final position is when Blades 124 reaches Hard Stop 126. In the final position, Blades 124 creates an enclosure, allowing Sample 134 on the object to be captured. It should be noted that in some embodiments that the force of expansion of Sampling Springs 104 pushes Blades 124 from the initial position to the final position in approximately 30-40 ms.

A pair of blade Carriage Rails 122 are used to allow Blades 124 to move (or glide) from an initial (or retracted) position to a final (or closed) position. Attached to each Blade 124 is an Overload Spring 120. Overload Springs 120 may prevent Blades 124, as well as the various components of BiBlade sampler 100, from damage when penetrating into the surface of the object. For instance, when Blades 124 penetrate the surface of the object, Overload Springs 120 may absorb the energy generated by the force released from Sampling Springs 104 and/or the energy generated by the impact with the surface of the object by Blades 124. Overload Springs 120 may also absorb impact energy when the Blades 124 impact the Hard Stops 126 in certain embodiments. Each Overload Spring 120 slides over a shaft on the end of a Blade 124 and compresses due to relative motion between a Blade 124 and a Carriage Bushing 116. The shaft at the end of a Blade 124 may have a spline shape and slide in a Carriage Bushing 116 with a corresponding spline shape. The spline shape of the Blade 124 shaft and Carriage Bushing 116 prevents the Blade 124 shaft from rotating in the Carriage Bushing 116. A Blade 124 is thus constrained to the linear motion of a Carriage 118 but with an Overload Spring 120 to relieve forces between a Blade 124 and its corresponding Carriage 118. Each Carriage Bushing 116 is part of a Carriage 118. Each Carriage 118 may move along a corresponding Carriage Rail 122, essentially moving Blades 124 from a retracted position to a closed position.

Hard Stops 126 may be used to stop Blades 124 at the closed position. Simply put, hard stops 126 may transfer the impact energy to a stronger structural element of BiBlade Sampler 100, preventing Blades 124 from self-destructing due to impact or interference.

Once Sample 134 is captured, Sample 134 may be constrained between a Retaining Lid 132 and between Blades 124 until deposited into a sample vault (not shown). In order to transfer Sample 134 to the sample vault, the robotic arm may insert the closed (or unretracted) Blades 124 into the sample vault. When Blades 124 may be retracted, Retaining Lid 132 may be released from BiBlade Sampler 100. Retaining Lid 132 may be captured by the top of the vault to retain Sample 134 in the vault. In some embodiments, multiple nested Retaining Lids 132 may be attached on BiBlade Sampler 100, and multiple sample vaults may be used to allow for capturing and storing multiple samples.

FIG. 2 is a cross-sectional view illustrating a Lid Assembly 200, according to an embodiment of the present invention. In some embodiments, Lid Assembly 200 includes a pair of Bolt Catchers 202 and a pair of Frangibolt Actuators 204. Bolt Catchers 202 may hold or retain Frangibolt 206 in place after Frangibolt 206 is released or fired. In order to release Retaining Lid 208, Frangibolt Actuators 204 may heat and/or fire Frangibolt 206 to release Retaining Lid 208 onto the sample vault. This may allow the Sample 134, once placed into the sample vault, to be secured.

Although not shown in detail, in some embodiments, the retaining lid is initially part of the sample vault, as opposed to the retaining lid initially being attached to the BiBlade sampler and then transferred to the vault. These embodiments may allow the BiBlade sampler to be used for Earth applications, e.g. undersea robotic sampling. It should be noted, however, that the number of returned samples may be limited by the number of sample vaults, and not the number of lids on the sampler. In some embodiments, one or more retaining lids may initially be attached to one or more sample vaults. The retaining lids may be configured to function similar to a guillotine, i.e., the retaining lid may slide over the top of the sample vault after the sample has been inserted and the blades of the BiBlade sampler are retracted. After closing the lid, the BiBlade sampler could be moved away and used to acquire another sample.

Returning to FIGS. 1A and 1B, Retaining Lid 132 may be affixed to Lid Assembly 130. Because BiBlade Sampler 100 may be used multiple times during a mission, more than one Retaining Lid 132 may be affixed to Lid Assembly 130.

FIG. 3 illustrates a process 300 for collecting a sample from an object, according to an embodiment of the present invention. In some embodiments, process 300 may begin at 302 with the blades of the BiBlade sampler being in a closed position. At 304, the Actuator on BiBlade sampler may load springs, that is push the gripper down to latch onto the Shuttle, and once latched on, pull the gripper in order to compress the springs and retract the blades. At 306, as the BiBlade sampler approaches the surface of the object, the BiBlade sampler waits to unload the springs. In some embodiments, the BiBlade sampler may unload the springs when the spacecraft is approximately 3 meters from the surface of the object and the robotic arm has deployed the BiBlade sampler to the surface. At 308, the motion of the Actuator causes the Gripper to move back to the release point and push down on the fingers of the Gripper to release the Shuttle. As the Shuttle is released, the springs are uncompressed causing the blades to penetrate the surface of the object to capture the sample. At 310, the Actuator causes the Gripper to travel down the Roller Screw and to latch onto the Shuttle, and at 312, the BiBlade sampler is pulled away from the surface of the object by spacecraft or robotic arm motion. The tapered configuration of the blades facilitate removal of the BiBlade sampler from the surface, since any linear motion away from the surface of the object would release the closed blade volume in all directions.

Figure 4:
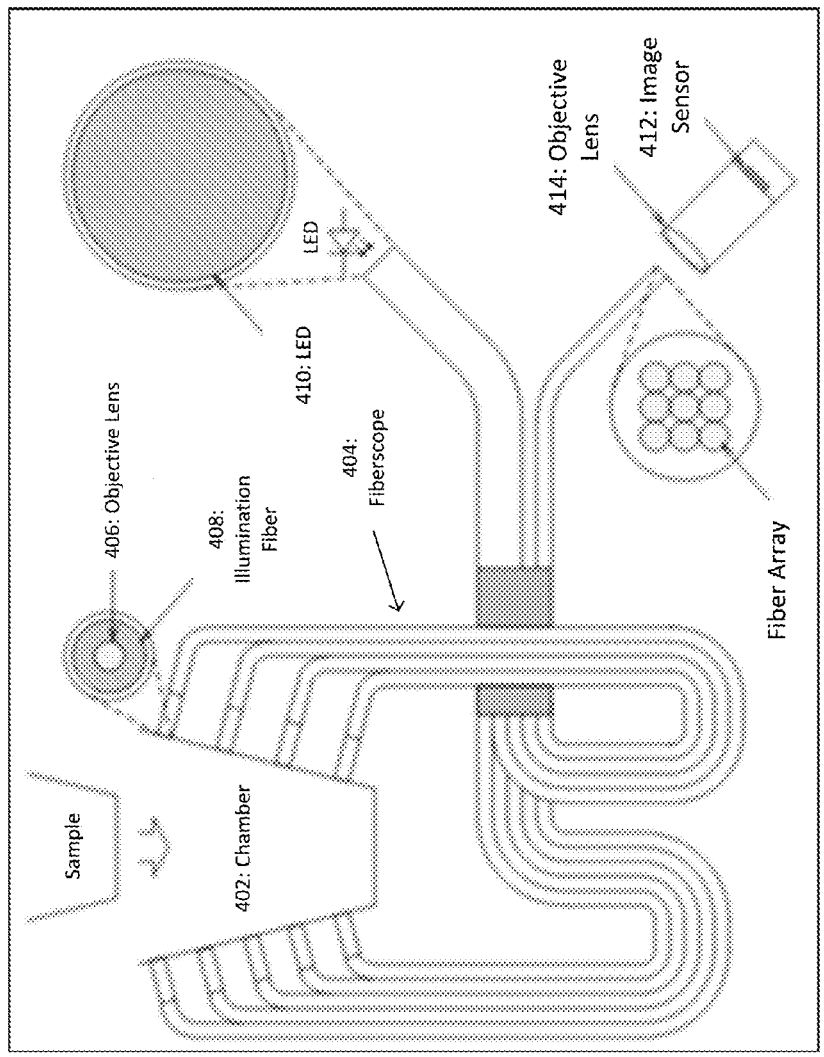
FIG. 4 is a cross-sectional view illustrating a measurement chamber, according to an embodiment of the present invention.
Figure 5:
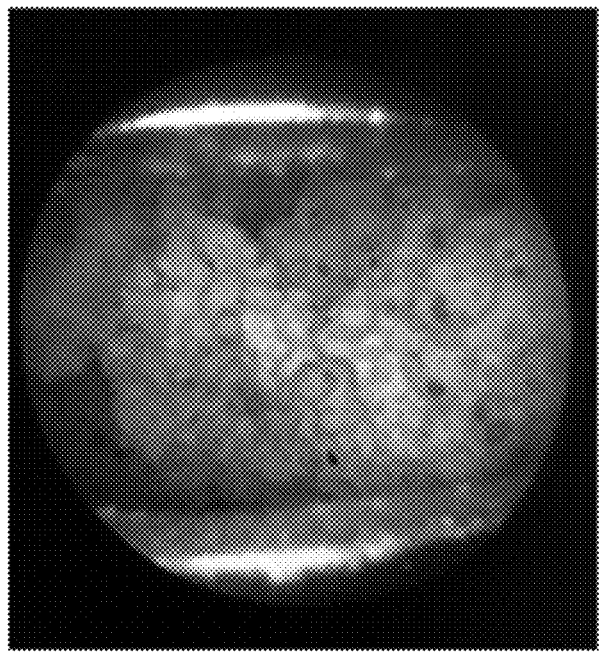
FIG. 5 illustrates an image of a captured sample, according to an embodiment of the present invention.

Once the sample of the object is captured, the sample may be taken to a sample measurement station. See, for example, FIG. 4, which is a cross-sectional view illustrating a Sample Measurement Station 400, according to an embodiment of the present invention. Sample Measurement Station 400 may include a Chamber 402, where the blades containing the sample are inserted. Sample Measurement Station 400 may include a plurality of Fiberscopes 404, and each Fiberscope 404 may include an Objective Lens (or Imaging Fiber) 406, which can view into Chamber 402, and an Illumination Fiber 408 to illuminate the sample within Chamber 402. Each Lens 406 may have a 55-degree field of view in some embodiments. The field of view allows for viewing a large area of the surface. Connected to each Fiberscope 404 is a Light Emitting Diode (LED) 410 providing light when capturing images of the sample enclosed within the blades. Also connected to each Fiberscopes 404 is an Image Sensor 412, which includes Objective Lens 414, to capture the image of the sample. In some embodiments, images may be in a parallelized configuration to enable a single camera and a light source. To capture the images of the sample, the BiBlade sampler may slightly retract the blades to create a slit between the blades. The slit may be as small as 5 mm in some embodiments. The slit may then expose the sample allowing Fiberscopes 404 to capture the images of the sample. For instance, the sample in some embodiments is illuminated by an Illumination Fibers 408 around the perimeter of each Fiberscopes 404. This allows Fiberscopes 404 to capture the image of the sample. See, for example, FIG. 5, which illustrate an image 500 of a captured sample, according to an embodiment of the present invention. After the sample measurement is complete, the blades may be closed, and the robotic arm may remove the sample enclosed within the blades from the sample measurement chamber. As discussed above, the robotic arm may then transfer the sample to a vault of the vehicle in some embodiments to complete the process of capturing, measuring, and storing the sample.

One or more embodiments generally pertain to a BiBlade sampler that includes two blades used to acquire and retain a sample. The sample may be extracted from the surface of an object. This object may include a comet, asteroid, moon, a planet, etc. The fast linear motion of the blades allows for the acquisition and retention of the sample. The resulting shape of the sample, which is formed by the two closed blades, may be tapered in all directions. The tapered blades would facilitate removal of the sampler from the surface of the object, since any linear motion away from the object would release the closed blade volume in all directions.

In an embodiment, the BiBlade sampler may be deployed to the surface of the object using a robotic arm. Once the BiBlade sampler is near the surface of the object, the blades are driven into the surface with springs in less than 0.1 seconds, for example. Once the sample is enclosed with the blades, the spacecraft, for example, would immediately thrust away from the object, thus retracting the BiBlade sampler from the object.

In certain embodiments, the BiBlade sampler may include two blades, which are attached to linear carriage rails by carriages. The carriages are connected to a shuttle using pushrods. The shuttle slides on two linear shafts. The shuttle is grasped or released by a gripper that is attached to the nut of a roller screw. The roller screw is driven by a rotary actuator. The nut is prevented from rotation using two additional rods. The gripper is passive in certain embodiments, and is able to grasp the shuttle when it is driven to the bottom end of the roller screw. The gripper may release the shuttle when the nut reaches the top end of the roller screw, closer to the actuator.

In preparation for sampling, the gripper fingers (or hooks) would be attached to the shuttle, and the actuator would pull the gripper back along the roller screw drive shaft. Full retraction of the actuator would cause the gripper to release the fingers to release the shuttle. This may cause the sampling springs to push the shuttle down its rails, and the shuttle may then transfer motion through the pushrods. The pushrods may then push the blades down their canted carriage rails and into the surface.

For later release of the sample, the gripper may be driven down the roller screw until the gripper grasps the shuttle. When the sample is released later in the sample vault of the Earth reentry vehicle, the shuttle may then be pulled back by the actuator as the sampling springs are compressed.

In yet some further embodiments, an imaging system may directly measure the sample. For example, the robotic arm may insert the BiBlade sampler with its closed blades enclosing the sample into a sample measurement chamber at a sample measurement station on the spacecraft. The blades may be pulled back slightly, exposing the sample in the slit between the blades. Multiple fiberscopes (or imagers) along the walls of the measurement chamber may passively transfer views of the surface of the sample to a common camera, which would acquire one picture that includes images from the fiberscope locations. The fiberscopes may be flexible and robust to the thermal environment, and transfer the images to a camera. The camera in some embodiments may be in a warm electronics box away from the measurement station. The sample may be illuminated by light emitted around the perimeter of the fiberscope optical elements. After sample measurement is complete, the blades may be closed and the robotic arm may remove the sample enclosed in the blades from the sample measurement station. If sample measurement is completed in sample vault of the Earth reentry vehicle, then the sample may be immediately deposited therein.

The acquired images provide direct measurement of the surface of the sample. It is assumed that there may be material internal to the sample. With the surface measurement and the assumption of material internal to the sample, the volume measurement can be made.

To store a sample for return to Earth, the robotic arm may transfer the sample enclosed in the blades to the Earth reentry vehicle by inserting the closed blades into a sample vault. Once inserted, the blades may be retracted leaving the sample behind in the sample vault. A lid attached to the sampler may be released and retained by the sample vault lid retaining clips, thus retaining the lid as well as the now encapsulated sample in the sample vault.

The BiBlade sampler may hold one or more lids, since there are one or more sample vaults on an Earth reentry vehicle. The lids may be in a nested configuration so that either lid could be used with either of the sample vaults. In some embodiments, lids may include a frangibolt and separation springs. For example, a set of separation springs may be positioned between the first and second lids, as well as between the BiBlade sampler body and the second lid. When the blades are inserted into the sample vault, retention clips attached at the top of the vault may deflect out of the way by the blades. The blades may then be retracted and the retention clips would spring back against the lid locking features, fully retaining the exposed lid. A frangibolt in some embodiments releases a lid from the BiBlade sampler and a spring would separate the lid from the BiBlade sampler. The lid may be retained at the top of the sample vault, also retaining the sample. The lid clips may be all around the perimeter at the top of the vault to ensure that lid is restrained and sample material could not escape from the sample vault. A second seal may further prevent any sample material from leaking out of the sample vault.

In certain embodiments, a sample may be rejected rather than stored when using the BiBlade sampler. For example, to reject a sample, the robotic arm may extend the sampler away from the spacecraft and the blades may then be fully retracted to expose the sample while the spacecraft thrusts away from the direction of the exposed sample. The spacecraft may move away from the sample and then the blades may be closed. Any material that remained with the sampler could be combined with the subsequent sample.

In an alternative embodiment, the BiBlade sampler may be used with percussive hammering as a way to deliver penetration energy. For example, the compression springs may be replaced with two percussive mechanisms. The percussive mechanism may use a constant impact energy such as a helical incline and a spring. A set of sliders may be attached to rails and controlled by a linear actuator using push rods. The blades and percussive actuators may be attached to these sliders using an interface that allows limited axial motion to the blade. For sampling purposes, the linear actuator may preload the blades against the sampling media and the percussive actuators hammer the back of the blade, significantly reducing required axial preload.

In yet another embodiment, a dual-shell configuration of the BiBlade sampler may be used to capture and retrieve a sample from the surface of an object. The dual-shell BiBlade sampler may have an inner and outer shell for each blade. During the sampling event, the blades may be driven into the surface of the object. At the completion of the sampling motion, the outer blades may be attached to a skirt that is initially attached to the body of the BiBlade sampler, nominally using a ratcheting capture mechanism. The inner blades are attached to a lid, also via a ratcheting mechanism.

After the sampling action is completed, the drive mechanism and skirt may be released from the deployment arm and the inner blades would be pulled away, attached to the robotic arm by the lid. The dual-shell configuration has the benefit that the motion of the inner blades is only relative to the outer blades and not relative to the comet surface, potentially improving the robustness of removal of the sampler from the comet surface relative to the single blade BiBlade design.

A passive ball-lock may be connected to the inner and outer shells, when the inner and outer shells are driven into the sampling material. In some embodiments, pneumatic cylinders, or springs, may be used to drive the blades into the stimulant material. After sampling, ball-locks may be retracted which passively release the inner and outer shells so that the inner and outer shells are no longer connected.

The inner shells are attached to the lid via a ratcheting mechanism with spring steel in a circular pattern on the shell attached to a ribbed post on the lid. The outer shells are attached to the skirt with a ratcheting mechanism. The integrated lid and inner shells with sample could then be removed by the robotic arm.

It will be readily understood that the components of various embodiments of the present invention, as generally described and illustrated in the figures herein, may be arranged and designed in a wide variety of different configurations. Thus, the detailed description of the embodiments, as represented in the attached figures, is not intended to limit the scope of the invention as claimed, but is merely representative of selected embodiments of the invention.

The features, structures, or characteristics of the invention described throughout this specification may be combined in any suitable manner in one or more embodiments. For example, reference throughout this specification to "certain embodiments," "some embodiments," or similar language means that a particular feature, structure, or characteristic described in connection with the embodiment is included in at least one embodiment of the present invention. Thus, appearances of the phrases "in certain embodiments," "in some embodiment," "in other embodiments," or similar language throughout this specification do not necessarily all refer to the same group of embodiments and the described features, structures, or characteristics may be combined in any suitable manner in one or more embodiments.

It should be noted that reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention can be practiced without one or more of the specific features or advantages of a particular embodiment. In other instances, additional features and advantages may be recognized in certain embodiments that may not be present in all embodiments of the invention.

One having ordinary skill in the art will readily understand that the invention as discussed above may be practiced with steps in a different order, and/or with hardware elements in configurations which are different than those which are disclosed. Therefore, although the invention has been described based upon these preferred embodiments, it would be apparent to those of skill in the art that certain modifications, variations, and alternative constructions would be apparent, while remaining within the spirit and scope of the invention. In order to determine the metes and bounds of the invention, therefore, reference should be made to the appended claims.

The invention claimed is:

1. An apparatus, comprising:
a first blade and a second blade in a retracted position; and
a gripper driven by an actuator, wherein
the gripper comprises a plurality of fingers to force the first blade and the second blade to remain in the retracted position, and when the fingers are unhooked, the first blade and the second blade penetrate a surface of an object,
wherein the actuator is configured to drive the gripper towards a shuttle, causing the gripper to passively lock onto the shuttle, and
wherein, when the gripper passively locks onto the shuttle, the actuator is further configured to pull the gripper and the shuttle, causing the first blade and the second blade to retract.

2. The apparatus of claim 1, wherein the shuttle comprises a plurality of grooves, allowing the plurality of fingers to lock onto the shuttle.

3. The apparatus of claim 2, wherein, when the gripper is pulled back to a predefined position, the actuator is configured to apply pressure to the plurality of fingers, unhooking the shuttle from the gripper.

4. The apparatus of claim 3, wherein the unhooking of the shuttle from the gripper allows the first blade and the second blade to move from the retracted position and into the surface of the object.

5. The apparatus of claim 1, wherein the pulling of the gripper and the shuttle causes a first sampling spring and a second sampling spring to compress.

6. The apparatus of claim 5, wherein, when the gripper releases the shuttle, the first sampling spring and the second sampling spring are expanded, and a force from the expansion causes the shuttle to move forward.

7. The apparatus of claim 6, wherein the forward movement of the shuttle causes the first blade and the second blade to move forward, penetrating the surface of the object.

8. The apparatus of claim 7, wherein the first blade and second blade move along a first carriage rail and a second carriage rail from the retracted position to a closed position and visa-versa.

9. A BiBlade sampler for a capturing a sample from an object, comprising: a gripper configured to latch on to a shuttle using a plurality of fingers; and an actuator configured to pull the shuttle to a release point, causing a set of blades to move to a retracted position, wherein the set of blades are connected to the shuttle via a set of pushrods, and when the shuttle reaches the release point, the plurality of fingers releases the shuttle, causing the set of blades to move to a final position.

10. The BiBlade sampler of claim 9, wherein the final position allows the set of blades to create an enclosure for encapsulating a sample from an object.

11. The BiBlade sampler of claim 9, further comprising:
a set of sampling springs configured to compress when the shuttle is pulled toward the release point, and decompress when the shuttle reaches the release point.

12. The BiBlade sampler of claim 11, wherein the decompression of the set of sampling springs causes a force to be exerted onto the set of blades, thereby moving the set of blades from the retracted position to the final position.

13. The BiBlade sampler of claim 9, further comprising:
a set of overload springs attached to the set of blades are configured to absorb energy generated when the set of blades penetrate a surface of the object.

14. The BiBlade sampler of claim 9, further comprising:
a set of hard stops configured to prevent the set of blades from moving beyond the final position, and transfer energy generated by impact with the set of blades to structural elements of the BiBlade sampler.

15. The BiBlade sampler of claim 9, wherein the shuttle comprises a plurality of grooves, allowing the plurality of fingers to latch onto the shuttle.

16. The BiBlade sampler of claim 9, wherein, when the shuttle reaches a release point, the actuator presses against the plurality of fingers, releasing the shuttle.

17. The BiBlade sampler of claim 9, further comprising:
a set of carriage rails allowing the set of blades to move between the retracted position and the final position.

18. The BiBlade sampler of claim 9, wherein the set of blades are attached to a set of overload springs, the set of overload springs absorb energy generated when the set of blades impact with a set of hard stops.

* * * * *